(12) United States Patent
Askeland

(10) Patent No.: US 12,350,140 B2
(45) Date of Patent: ***Jul. 8, 2025

(54) VARIABLE LENGTH STENT

(71) Applicant: Sevro Technologies LLC, Cedar Falls, IA (US)

(72) Inventor: Eric Askeland, Cedar Falls, IA (US)

(73) Assignee: Sevro Technologies LLC, Cedar Falls, IA (US)

( * ) Notice: Subject to any disclaimer, the term of this patent is extended or adjusted under 35 U.S.C. 154(b) by 565 days.

This patent is subject to a terminal disclaimer.

(21) Appl. No.: 17/324,730

(22) Filed: May 19, 2021

(65) Prior Publication Data

US 2021/0267747 A1    Sep. 2, 2021

Related U.S. Application Data

(63) Continuation of application No. 16/504,511, filed on Jul. 8, 2019, now Pat. No. 11,039,914.

(60) Provisional application No. 62/748,627, filed on Oct. 22, 2018.

(51) Int. Cl.
*A61F 2/04* (2013.01)
*A61F 2/95* (2013.01)

(52) U.S. Cl.
CPC .......... *A61F 2/04* (2013.01); *A61F 2002/048* (2013.01); *A61F 2002/9511* (2013.01); *A61F 2230/0091* (2013.01); *A61F 2250/0007* (2013.01); *A61F 2250/0097* (2013.01)

(58) Field of Classification Search
None
See application file for complete search history.

(56) References Cited

U.S. PATENT DOCUMENTS 4,531,933 A * 7/1985 Norton ............... A61B 90/39
604/8
4,643,716 A    2/1987 Drach
4,790,810 A    12/1988 Pugh, Jr. et al.
(Continued)

FOREIGN PATENT DOCUMENTS

GB    2132091 A    7/1984
JP    S59111748 A    6/1984
(Continued)

OTHER PUBLICATIONS

International Search Report and Written Opinion dated Oct. 2, 2019 from related International Patent Application No. PCT/US2019/040761.

(Continued)

*Primary Examiner* — Leslie A Lopez
(74) *Attorney, Agent, or Firm* — SHUTTLEWORTH & INGERSOLL, PLC; Jason R. Sytsma

(57) ABSTRACT

A stent comprising a tubular member, a lumen extending through the tubular member, a first retention structure and a second retention structure at opposite ends of the tubular member. The first retention structure comprises multiple coils and a removable anti-coiling material over the multiple coils of the first retention structure to present the multiple coils as an elongated extension of the tubular member, whereupon removal of the removable anti-coiling material at least one of the multiple coils of the first retention structure is presented and any excess coils can be trimmed.

19 Claims, 10 Drawing Sheets

(56) References Cited

U.S. PATENT DOCUMENTS

| | | | |
|---|---|---|---|
| 4,813,925 A * | 3/1989 | Anderson, Jr. | ............ A61F 2/88 604/93.01 |
| 4,820,262 A | 4/1989 | Finney | |
| 5,380,270 A | 1/1995 | Ahmadzadeh | |
| 5,523,092 A * | 6/1996 | Hanson | ..................... A61F 2/06 604/523 |
| 5,647,843 A | 7/1997 | Mesrobian et al. | |
| 5,681,274 A | 10/1997 | Perkins et al. | |
| 5,964,744 A | 10/1999 | Balbierz et al. | |
| 6,582,472 B2 | 6/2003 | Hart | |
| 6,685,744 B2 | 2/2004 | Gellman et al. | |
| 6,991,614 B2 | 1/2006 | McWeeney et al. | |
| 7,037,345 B2 | 5/2006 | Bottcher et al. | |
| 7,044,981 B2 | 5/2006 | Liu et al. | |
| 7,507,218 B2 | 3/2009 | Aliski et al. | |
| 7,550,012 B2 | 6/2009 | Lavelle | |
| 7,674,283 B2 | 3/2010 | Mitchell et al. | |
| 7,789,915 B2 | 9/2010 | Lavelle et al. | |
| 8,328,877 B2 | 12/2012 | Gellman | |
| 8,568,643 B2 | 10/2013 | Gellman | |
| 9,060,888 B2 | 6/2015 | Gellman | |
| 9,763,814 B2 | 9/2017 | Biltz et al. | |
| 2004/0059279 A1 | 3/2004 | McWeeney et al. | |
| 2004/0087886 A1 | 5/2004 | Gellman | |
| 2004/0181186 A1 | 9/2004 | Gellman et al. | |
| 2008/0183299 A1 | 7/2008 | Monga et al. | |
| 2010/0070047 A1 | 3/2010 | Smouse | |
| 2010/0268314 A1 * | 10/2010 | Nowak, Jr. | ................ A61F 2/95 623/1.11 |
| 2014/0358245 A1 | 12/2014 | Harrah et al. | |
| 2016/0045347 A1 | 2/2016 | Smouse et al. | |
| 2016/0302857 A1 * | 10/2016 | Rothman | ............ A61B 18/1492 |
| 2017/0319324 A1 | 11/2017 | Ponsky et al. | |
| 2018/0125684 A1 | 5/2018 | DeGraaf et al. | |
| 2018/0161557 A1 | 6/2018 | DeGraaf et al. | |
| 2018/0193174 A1 | 7/2018 | Pendleton et al. | |

FOREIGN PATENT DOCUMENTS

| | | |
|---|---|---|
| JP | H1052500 A | 2/1998 |
| JP | H11501550 A | 2/1999 |
| JP | 2000500669 A | 1/2000 |
| JP | 2002537893 A | 11/2002 |
| WO | 9630070 A1 | 10/1996 |

OTHER PUBLICATIONS

Japanese Office Action dated May 31, 2022 from related Japanese Patent Application No. 2021-548503.

* cited by examiner

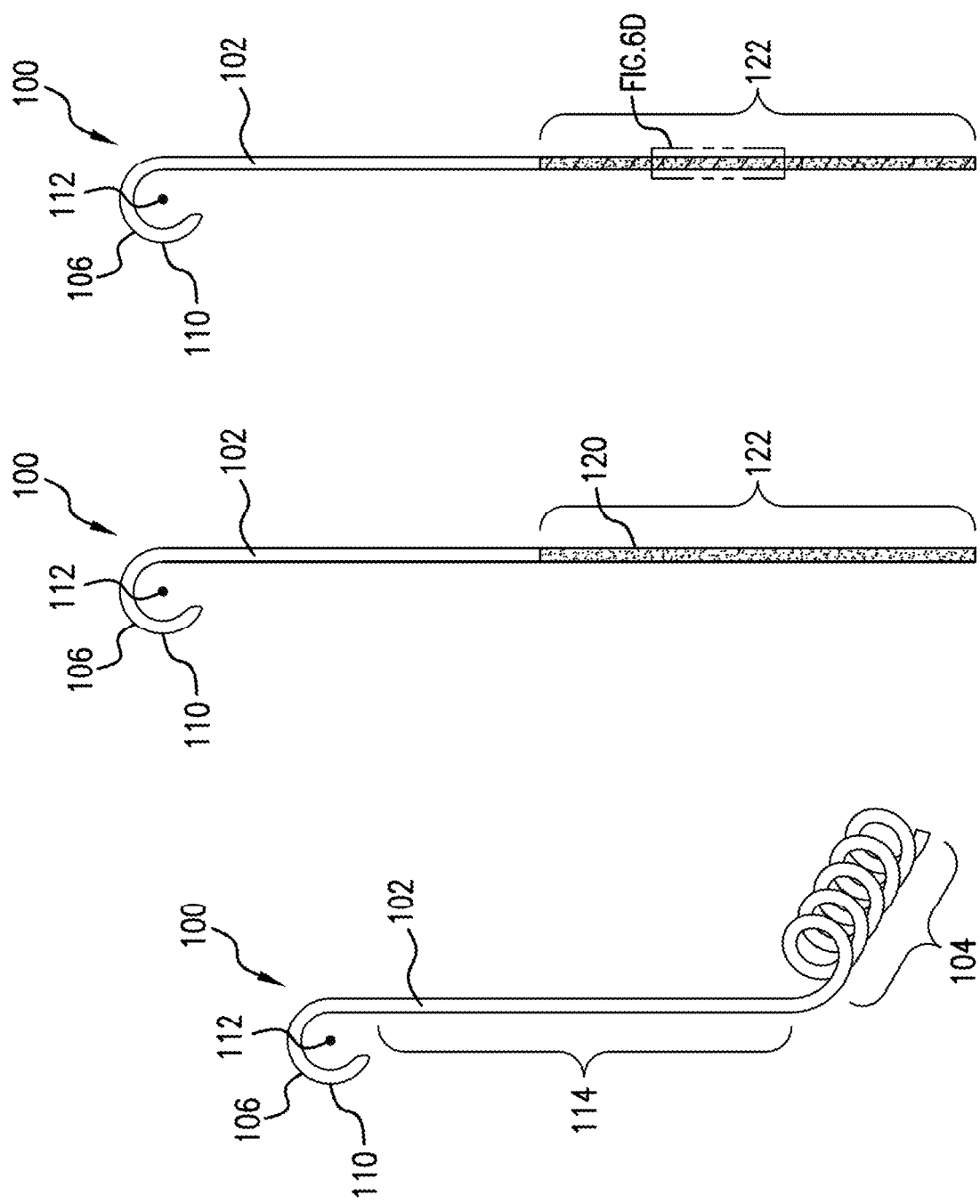

VARIABLE LENGTH STENT

CROSS-REFERENCE TO RELATED APPLICATIONS

The present application is a continuation of, and claims priority to and benefit of co-pending claims the benefit of U.S. Non-provisional application Ser. No. 16/504,511 entitled "Variable Length Stent," filed Jul. 8, 2019, which claimed priority from U.S. Provisional Patent Application No. 62/748,627 filed Oct. 22, 2018, the contents of which are incorporated herein by reference.

TECHNICAL FIELD

This disclosure generally relates to medical stents and particularly to variable length stents.

BACKGROUND INFORMATION

Stents are well known and widely accepted as viable prostheses for bypassing obstructions and promoting drainage. Ureteral stents, for example, function as a drainage tube between the renal pelvis of the kidney and the bladder. As the use of such stents has continued, it has been found that various applications require stents of different diameters. Moreover, differences in individual anatomies require stents having different effective lengths between the end retention structures, such as the curved and helical coil portions located at the bladder and kidney ends of the stent as shown in the prior art. Consequently, hospitals and other facilities inventory stents of different diameters and for each diameter, stents of different lengths.

Referring to FIG. 1, a coronal view of a ureteral stent 11 of the prior art positioned in a renal pelvis 14 of a kidney 10 and a bladder 20 of a person is shown. Kidney 10 drains urine into the renal pelvis 14, down the ureter 18, out of the ureteral orifice 17, and into the bladder 20. During placement of ureteral stent 11, a guide wire (not shown) is navigated through a cystoscope (not shown), through the ureteral orifice 17, beyond any obstruction in ureter 18, into the renal pelvis 14 of kidney 10. Stent 11 is then passed over this guidewire into the correct position at which point the guidewire is removed and the stent 11 is left in place. Stent 11 comprises a hollow tube that facilitates passage over the guidewire.

Stent 11 is designed with a bladder retention coil 24 for retaining stent 11 in the bladder 20 and a kidney retention coil 22 for retaining the stent 11 in renal pelvis 14 of kidney 10. The area of stent 11 between bladder retention coil 24 and kidney retention coil 22 is an intermediate portion 25. This is the non-coiled portion of the stent 11 that varies in length.

Hospitals inventory ureteral stents of differing lengths dictated by the non-coiled intermediate portion 25. The surgeon must choose the desired length prior to placement of stent 11. Stent 11 is also designed with a tapered tip 13 on a proximal portion 32 of kidney retention coil 22 that facilitates passage of stent 11 beyond any obstructive pathology in ureter 18. A distal portion 15 of bladder retention coil 24 is designed with at least one hole 16 for phishing a retrieval string 35 to attach retrieval string 35 to distal portion 15 of bladder retention coil 24. Retrieval string 35 is often left emanating from the patient's urethra 38 and can be extracted by the patient after a predetermined period of time. Retrieval string 35 is typically only utilized following treatment of the obstructive process.

Stent 11 is generally designed with a fixed diameter and fixed length that the surgeon must choose at the time of the procedure. Different diameters are chosen for various reasons at the surgeon's discretion based on preference and certain pathologic processes. The length of stent 11 is chosen based on the ureteral length. Often a patient's height is used as a surrogate to estimate the desired length. If stent 11 is too short, stent 11 will not span the entirety of ureter 18 and results in inadequate drainage of kidney 10. If stent 11 is too long, there is too much foreign material in either renal pelvis 14 or bladder 20 resulting in additional stent symptomatology including flank discomfort, urinary urgency, urinary frequency, urinary incontinence and hematuria. To rectify placement of a stent 11 of inappropriate length the surgeon must remove stent 11 and place a new stent 11 of the appropriate length resulting in additional operating room costs.

Though not an all-inclusive list, typical diameters for ureteral stents are 4.5, 6, 7 or 8 French (of the French Scale or French gauge). Likewise, though not all-inclusive, typical lengths of stents are 16, 18, 20, 22, 24, 26 or 28 cm. In order for hospitals to carry a full complement of stents, they must inventory stents with a combination of these diameters and lengths. These stents are manufactured with an expiration date, thus hospitals often will not carry stents in the extremes of length for fear of expiration prior to usage. This poses a clinical problem for physicians since often patients present to the emergency room needing urgent decompression of an obstructed system. If a stent of an extreme of length is anticipated the procedure may not be performed at the facility if they do not inventory these sizes. Certainly, a hospital can special order stents of a particular size, but usually the clinical situation does not provide the hospital enough lead-time to do this in a clinically useful timeframe. Furthermore, there are even more drastic extremes of length that would occasionally be useful to physicians but are almost universally not inventoried. Patients with a pelvic kidney or transplanted kidney would potentially benefit from even shorter ureteral stents. Conversely, patients with a tortuous ureter secondary to long-term obstruction may benefit from an even longer ureteral stent to accommodate the tortuosity of the ureter.

Multiple inventions have been patented to create a variable length ureteral stent. However, the majority of these designs rely on a redundancy of stent material that is left indwelling at the time of the procedure. As described above, any redundancy of stent material left indwelling may result in additional patient discomfort. Other designs are over-engineered or are fundamentally different from a typical ureteral stent design as to not be truly clinically useful.

Accordingly, there is a need for a ureteral stent with a completely modifiable length and the ability to trim redundant stent material. This affords the physician the ability to intraoperatively place a stent of the ideal length, using a single product, for every patient. The invention also significantly decreases hospital stent inventory, since only varied stent diameter would need to be inventoried. It has the added benefit of being able to accommodate ureteral lengths at the extremes that almost universally are not inventoried by hospitals.

SUMMARY

A stent comprising a tubular member, a lumen extending through the tubular member, a first retention structure and a second retention structure at opposite ends of the tubular member is disclosed. The first retention structure further comprises multiple coils each of which can have substantially the same diameter to provide an anchor for the stent. The stent can include a removable anti-coiling material over the multiple coils of the first retention structure to present the multiple coils as an elongated extension of the tubular member, whereupon removal of the removable anti-coiling material at least one of the multiple coils of the first retention structure is presented and any excess coils can be trimmed. The multiple coils can each be wound about a separate axis or a common axis to provide an anchor for the stent.

The stent can also include multiple indices on the elongated extension of the tubular member each of which demarcate a corresponding one of the multiple coils of the first retention structure. The multiple indices may each be circumferential perforations in the anti-coiling material that enables a stripping away of the anti-coiling material. The multiple indices may each be visual markings.

The anti-coiling material may be adapted for removal beginning from one of the multiple indices to an end of the elongated extension of the tubular member to present at least one coil of the multiple coils of the first retention structure. In which case one or more of the multiple coils is trimmable at a predetermined location to remove at least one coil from the multiple coils of the first retention structure to present a single coil of the multiple coils of the first retention structure.

The stent may also include a distal end on the second retention structure and a tapered tip on the distal end adapted for maneuvering the second retention structure past an obstruction. The distal end can also include an eyelet on the distal end of the tapered tip for receiving a suture.

BRIEF DESCRIPTION OF THE DRAWINGS

These and other features and advantages of the present invention will be better understood by reading the following detailed description, taken together with the drawings wherein:

FIG. 6A shows stent with a tubular member constructed in accordance with this disclosure.

FIG. 6B shows the stent of FIG. 6A with an anti-coiling layer to straighten the end.

FIG. 6C shows the stent of FIG. 6B with a series of circumferential perforations through the anti-coiling layer.

FIG. 6D is a close-up view of area 6D in FIG. 6C.

DETAILED DESCRIPTION OF THE PREFERRED EMBODIMENTS

Figure 2A:
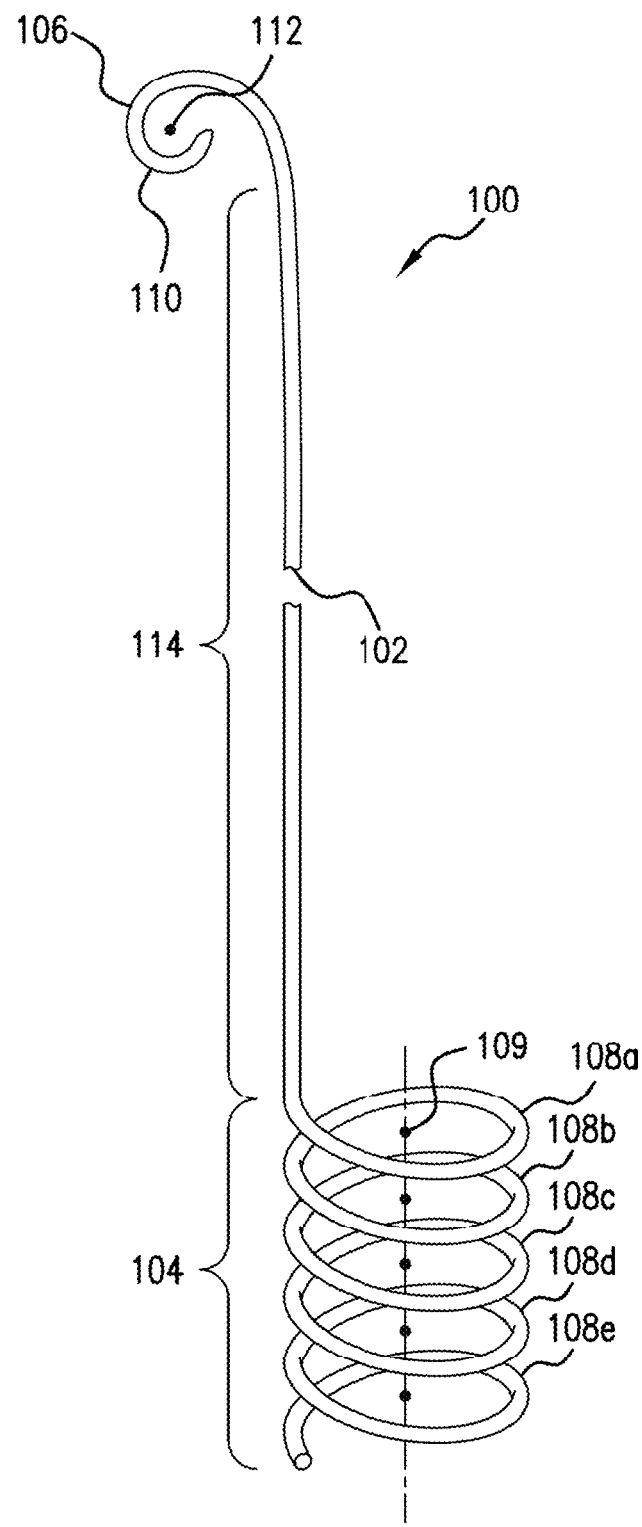
FIG. 2A is a perspective view of a stent with a tubular member constructed in accordance with this disclosure.

FIG. 2A is a perspective view of a stent 100 comprising a tubular member 102 and a lumen 103 (see FIG. 4) extending through the tubular member 102. At opposite ends of tubular member 102 are a first retention structure 104 and a second retention structure 106 with an intermediate portion 114 extending between the two. First retention structure 104 and second retention structure 106 are used to position one end of stent 100 in the renal pelvis of the kidney and the other end of stent 100 in the bladder with intermediate portion 114 extending in the ureter to prevent migration of stent 100 out of these areas.

First retention structure 104 is formed by bending an end of tubular member 102 into multiple coils 108. The illustrated embodiment shows five coils 108a-108e, but any number of coils 108 can be included. One skilled in the art would also recognize that at least two coils 108a, 108b is preferred. Multiple coils 108 are each formed by shaping the end of tubular member 102 into multiple spiral coils each having the same diameter and wound about an axis 109 to provide an anchor for stent 100. It could also be possible, however, to form multiple coils 108 by shaping the end of tubular member 102 into a multiple turn, spiral planar coil formed with multiple turns wound upon each other within the same plane about the same or common axis. This implementation leads to coils having increasingly larger diameters, but leads to more material inside the body.

Second retention structure 106 is formed by bending an end of tubular member 102 into a coil 110 around an axis 112. Coil 110 is formed by shaping the end of tubular member 102 in a turn. It could also be possible to form second retention structure 106 with multiple coils in the manner described above so that each end of tubular member 102 has multiple coils.

The first coil 108a of multiple coils 108 of first retention structure 104 and coil 110 of second retention structure 106 have the same construction. Each structure is formed around its respective axes 109, 112 that is orthogonal to and offset from an axis extending through intermediate portion 114 of stent 100 in the direction of flow. Thus, first coil 108a of first retention structure 104 and coil 110 of second retention structure 106 are offset from the axis extending through intermediate portion 114 and lead tangentially into intermediate portion 114 on opposite sides. Moreover, while first coil 108a of first retention structure 104 and coil 110 of second retention structure 106 can lie in a single plane that is common with intermediate portion 114, second coil 108b, third coil 108c, fourth coil 108d, and fifth coil 108e can lie in successively offset planes so that each of the multiple coils 108 can have a substantially similar diameter. A substantially similar diameter is defined as a diameter that is generally less than two times the outer diameter of tubular member 102, which is the overall diameter increase if a successive coil was coiled around an inner coil.

Figure 2B:
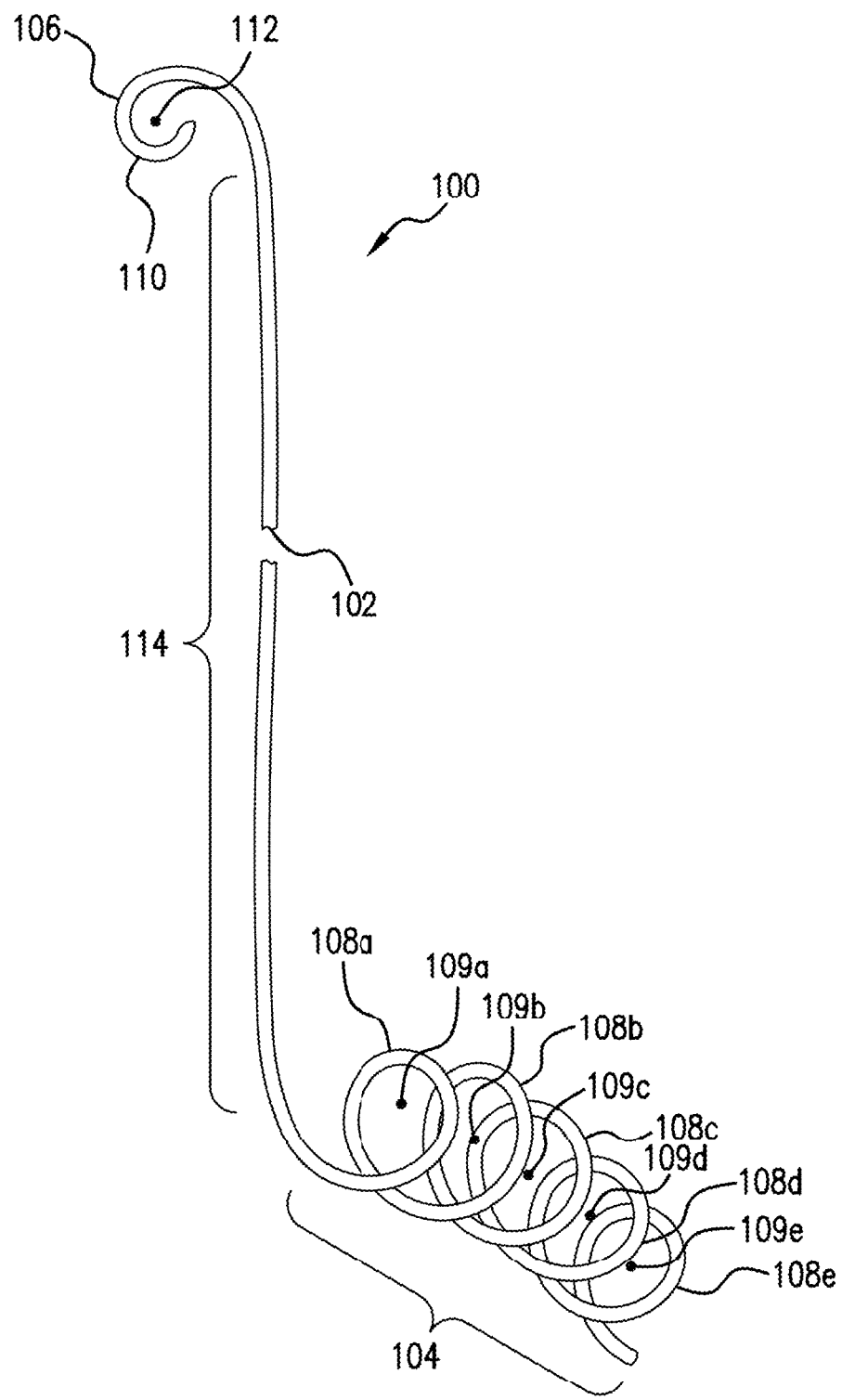
FIG. 2B is a perspective view of a stent with a tubular member also constructed in accordance with this disclosure.

FIG. 2B shows another example of a stent 100 comprising a tubular member 102 and a lumen 103 extending through the tubular member 102. At opposite ends of tubular member 102 are a first retention structure 104 and a second retention structure 106 with an intermediate portion 114 extending between the two. First retention structure 104 is formed by bending an end of tubular member 102 into multiple coils 108. The illustrated embodiment shows five coils 108a-108e wound about separate, unique axes 109a-109e. Multiple coils 108 are each formed by shaping the end of tubular member 102 into multiple spiral coils of the same diameter each wound about separate axes 109a-109e to provide an anchor for stent 100.

Figure 3:
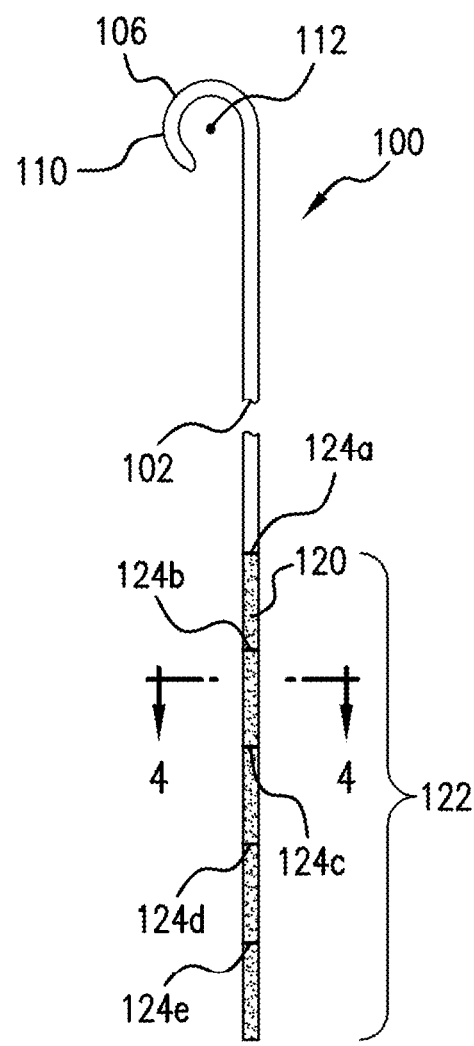
FIG. 3 is a perspective view of the stent of FIGS. 2A and 2B with an anti-coiling material applied over a retention structure to present the retention structure as an elongated extension of the hollow tubular member.

FIG. 3 shows stent 100 constructed in accordance with this disclosure that also includes an anti-coiling layer 120 over first retention structure 104 to present multiple coils 108 as an elongated extension 122 of tubular member 102. This allows the surgeon to use a stent stripper 200 (shown in FIG. 5B) intraoperatively to remove a segment of anti-coiling layer 120 resulting in stent 100 of a desired length but with at least one coil 108e of multiple coils 108a-108e. As shown in FIG. 5B, stent stripper 200 placed in position where a stripping action in the direction of the arrows will remove the corresponding portion of anti-coiling layer 120. Any redundant coils 108b-108e can then be trimmed using scissors in the operating room resulting in a stent of the desired length with minimal redundant indwelling stent-material. In this manner, if only a small portion of the anti-coil polymer 120 is removed, stent 100 could accommodate a very tall patient. Likewise, if the majority of the anti-coiling layer 120 is removed, and the resultant redundant coils 108b-108e are trimmed off, stent 100 could accommodate a pediatric patient or a patient of short stature.

In accordance with an aspect of this disclosure, multiple indices 124a-124e are spaced along elongated extension 122 of tubular member 102 that correspond with coils 108a-108e of multiple coils 108 on first retention structure 104. Indices 124a-124e enable the physician to determine the extent to which multiple coils 108 in first retention structure 104 unwrap when the corresponding amount of anti-coiling layer 120 is removed.

Figure 4:
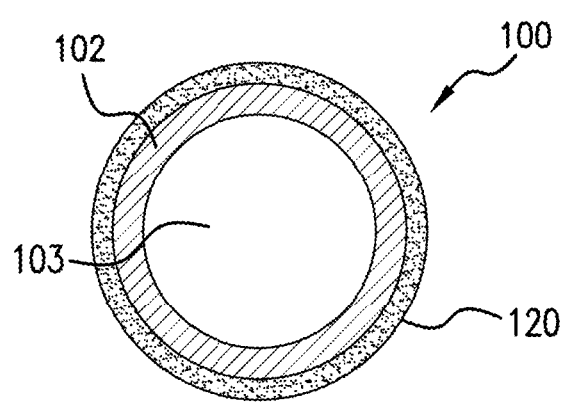
FIG. 4 is an enlarged cross-sectional view taken along the lines 4-4 in FIG. 3.

FIG. 4 shows a cross section of the stent 100 with the anti-coiling layer 120. The tubular member 102 surrounds lumen 103. The anti-coiling layer 120 coats a portion corresponding to elongated extension 122 of tubular member 102.

Figure 5D:
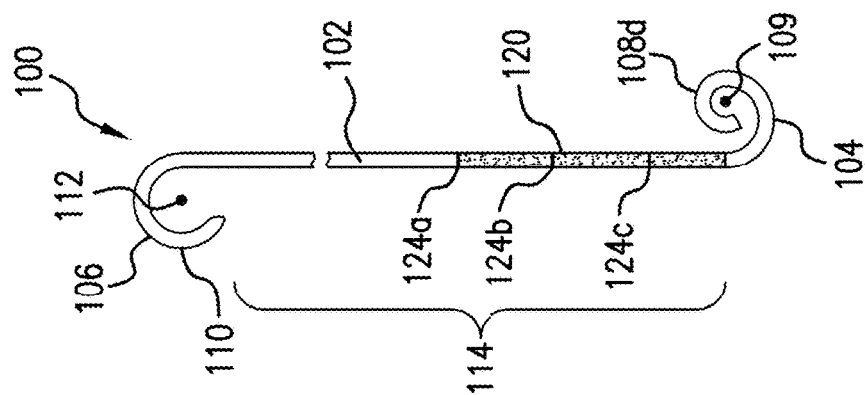
FIG. 5D is a perspective view of the stent of FIG. 5C showing the excess coils removed.
Figure 5C:
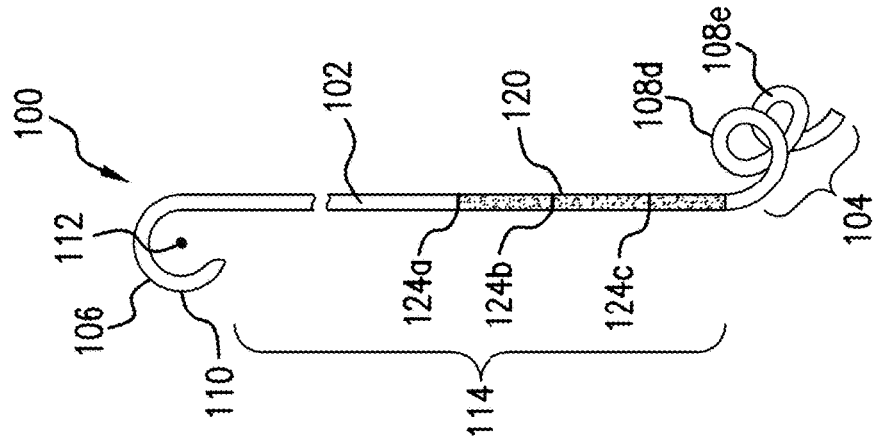
FIG. 5C is a perspective view of the stent of FIG. 5B showing the anti-coiling material removed.
Figure 5B:
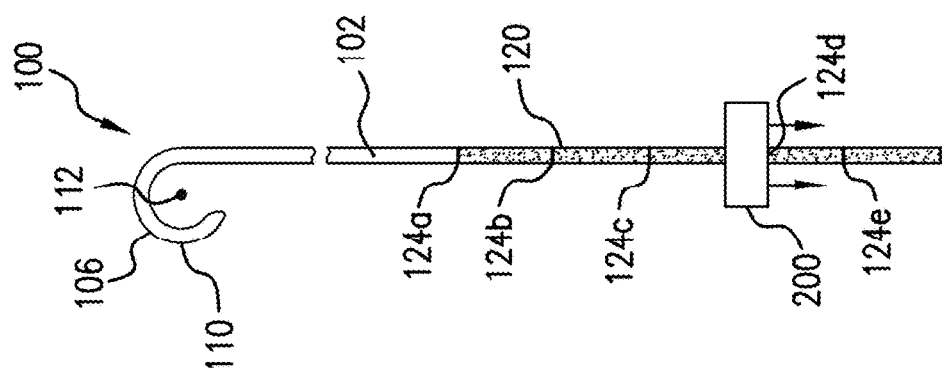
FIG. 5B is a perspective view of the stent of FIG. 5A showing a stripper to remove the anti-coiling material at a pre-determined location on the elongated extension of the tubular member.
Figure 5A:
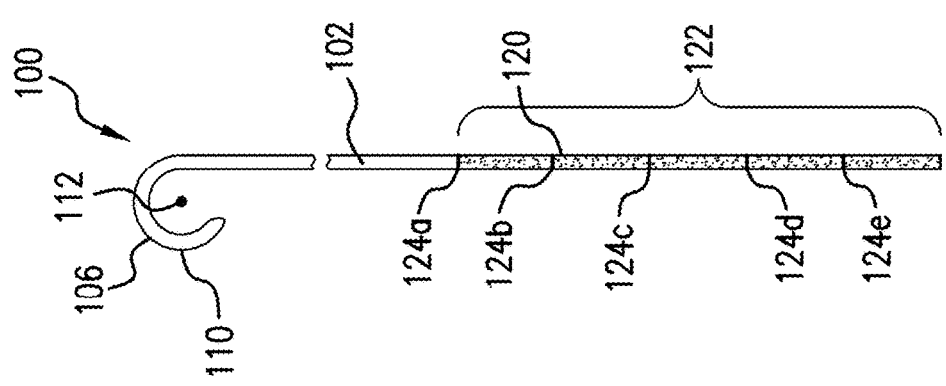
FIG. 5A is a perspective view of the stent of FIG. 3.

FIGS. 5A-5D shows the above-described process more clearly. FIG. 5A shows a perspective view of stent 100 as it would appear out of its packaging. Stent 100 presents second retention structure 106 at one end with tubular member 102 extending between second retention structure 106 and elongated extension 122 of tubular member 102 at the other end. The surgeon approximates the desired length of stent 100 with reference to the corresponding indices 124a-124e and positions a stent stripper 200 in the appropriate position, as shown in FIG. 5B. Stent stripper 200 creates a circumferential cut through anti-coiling layer 120 without penetrating tubular member 102. Anti-coiling polymer 120 is removed beginning at the location of the cut through the end of first retention structure 104 leaving at least one coil 108e of multiple coils 108, or in the illustrated process coils 108d and 108e of multiple coils 108. In this situation, coil 108e is a redundant coil, as shown in FIG. 5C. The physician then uses standard operating room scissors to trim redundant coil 108e to create the desired length of stent 100. The remaining stent 100 is the desired length with a single, standard coil 108d on first retention structure 104.

Figure 6G:
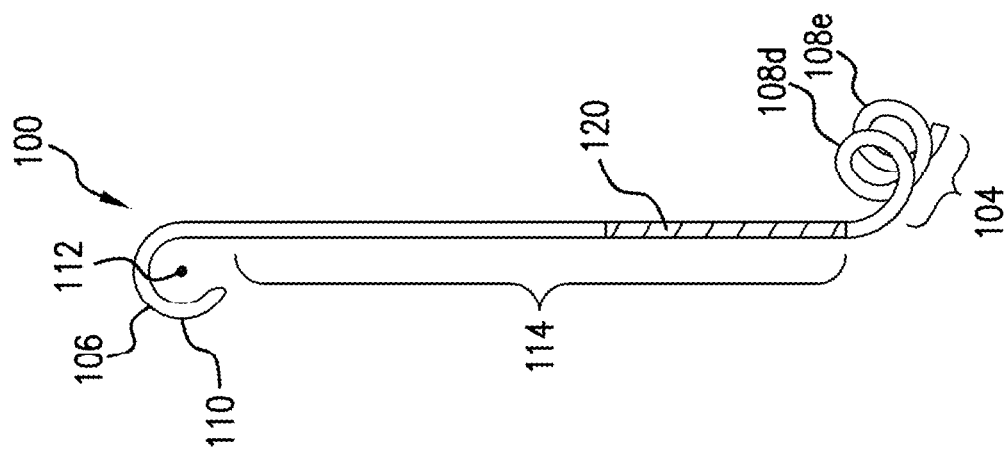
FIG. 6G shows the stent of FIG. 6E with a portion of the anti-coiling layer removed.
Figure 6F:
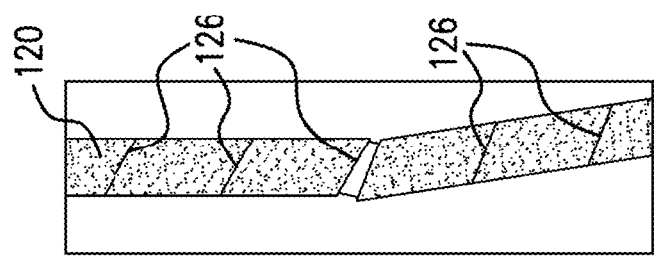
FIG. 6F is close-up view of area 6D of FIG. 6E.
Figure 6E:
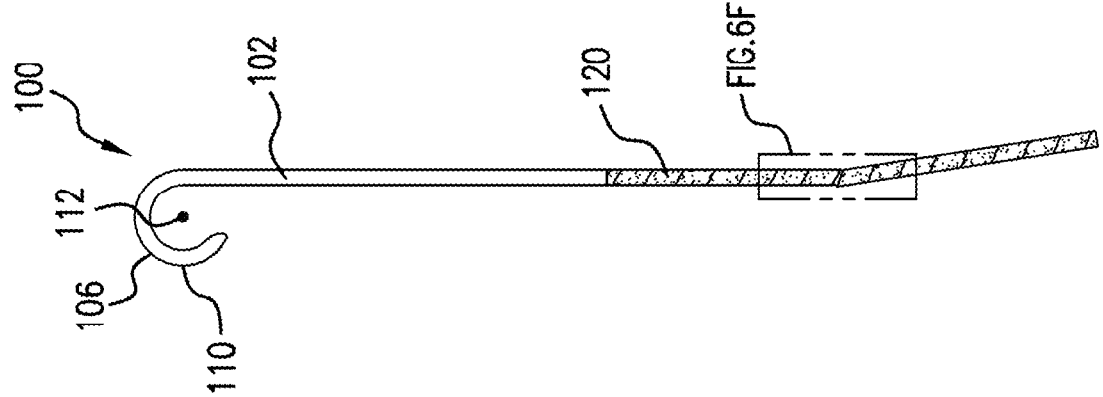
FIG. 6E shows the stent of FIG. 6C bent to break one of the series of circumferential perforations.

Indices 124a-124e can be visual markings along stent 100 for locating a stent stripper 200 or, as shown in FIG. 6C-6D, they could be a series of circumferential perforations 126 of a predetermined thickness. These circumferential perforations 126 would allow the surgeon to remove the anti-coiling layer 120 at the predetermined location. This implementation is similar to the proceeding where FIG. 6A shows stent 100 before anti-coiling layer 120 is applied and FIG. 6B shows stent 100 with anti-coiling layer 120. Anti-coiling polymer 120 is circumferentially perforated at predetermined intervals. These circumferential perforations 126 of anti-coiling layer 120 can be stripped from the stent manually at one of the premade circumferential perforations 126 rather than requiring stent stripper 200. The physician then manually strips anti-coiling layer 120 off of the remaining length of stent 100. By removing the anti-coiling layer 120, the end for first retention structure 104 of stent 100 presents coil 108d as first retention structure 104 with redundant coil 108e being trimmed off by the surgeon, as discussed above.

Figure 1:
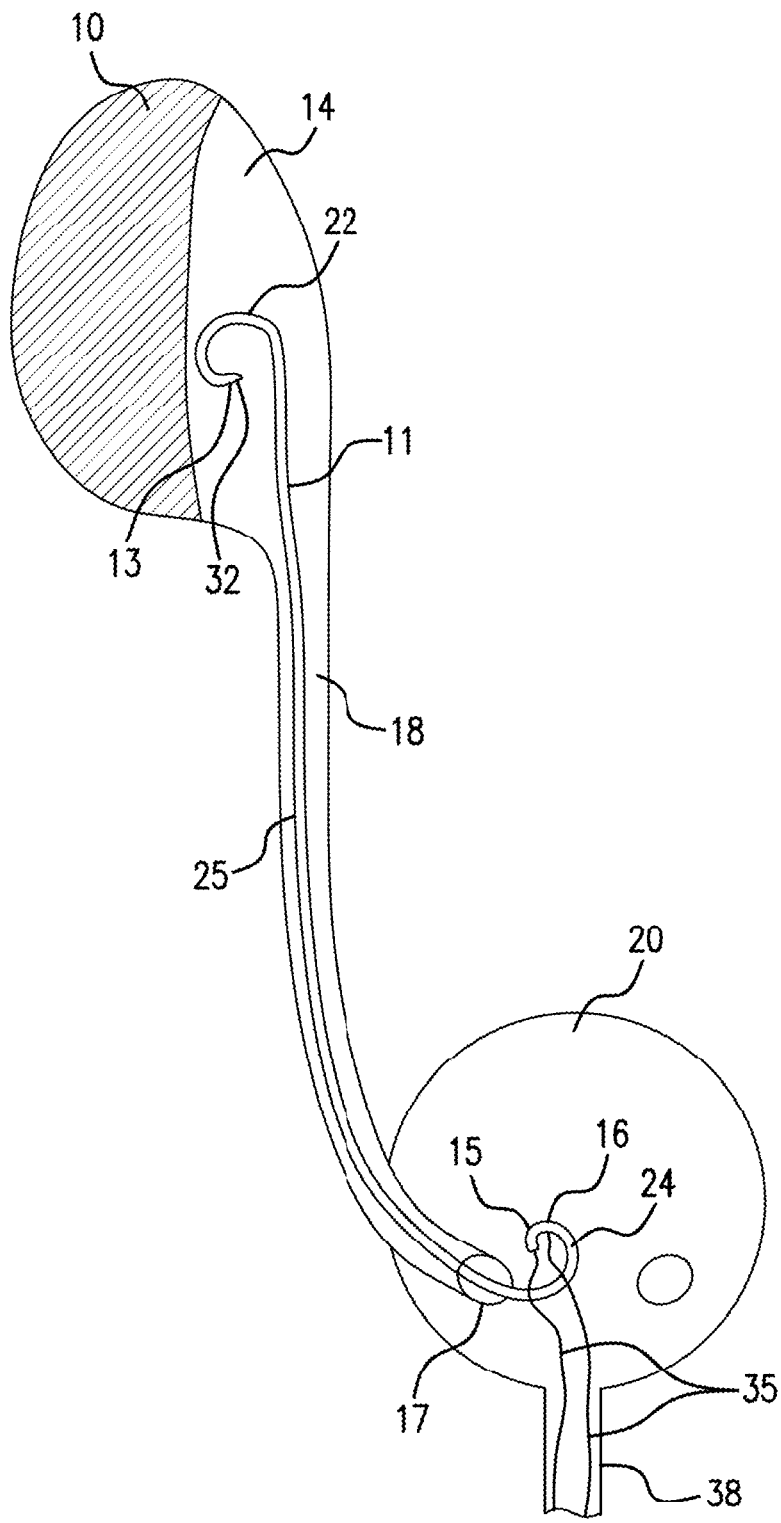
FIG. 1 is a coronal view of a ureteral stent of the prior art positioned in a renal pelvis of a kidney and a bladder of a person.

As described in FIG. 1, stent 11 of the prior art is designed in a polarized fashion with tapered tip 13 on the proximal portion 32 that facilitates passage beyond the obstructive pathology in ureter 18. Distal portion 15 is generally designed with retrieval string 35 attached to bladder retention coil 24. This retrieval string 35 is left emanating from urethra 38 and can be extracted by the patient at a predetermined period of time. Clinically, these two features are rarely utilized together in any individual surgical case. These two features are used separately depending on the procedure. As an example, if a patient with an obstructive ureteral stone presents with sepsis the patient needs urgent ureteral stent placement. In this case, tapered tip 13 is useful for navigating stent 11 beyond the obstructive process. Retrieval string 35 would not be utilized because the patient would need a second procedure to treat the stone after the infection has resolved. This second procedure usually involves ureteroscopic manipulation with fragmentation and removal of the stone. Ureteroscopic manipulation can cause postoperative ureteral swelling which can result in transient ureteral obstruction. For this reason, a ureteral stent is often left postoperatively. In this case, tapered tip 13 is not necessary since the primary obstructive process is resolved, but retrieval string 35 can be useful for removal of stent 11 after ureteral swelling has resolved.

Figure 7A:
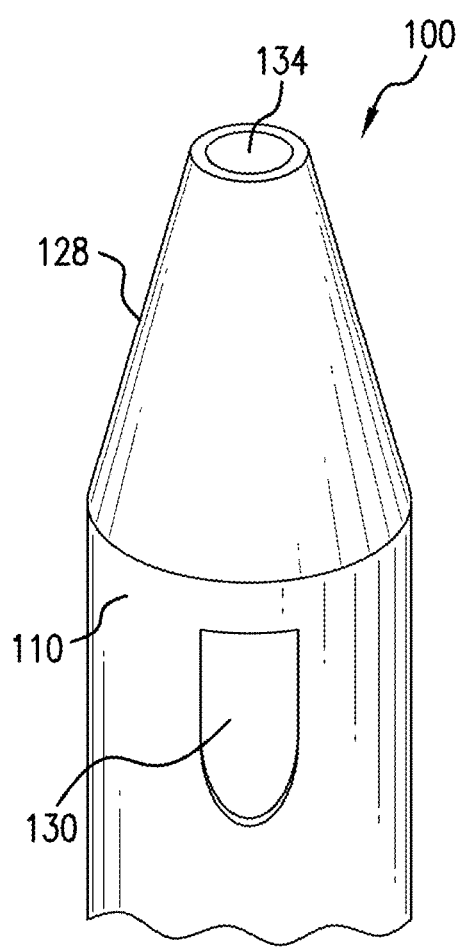
FIG. 7A is a close-up view of the second retention structure of the stent of FIG. 2.
Figure 7B:
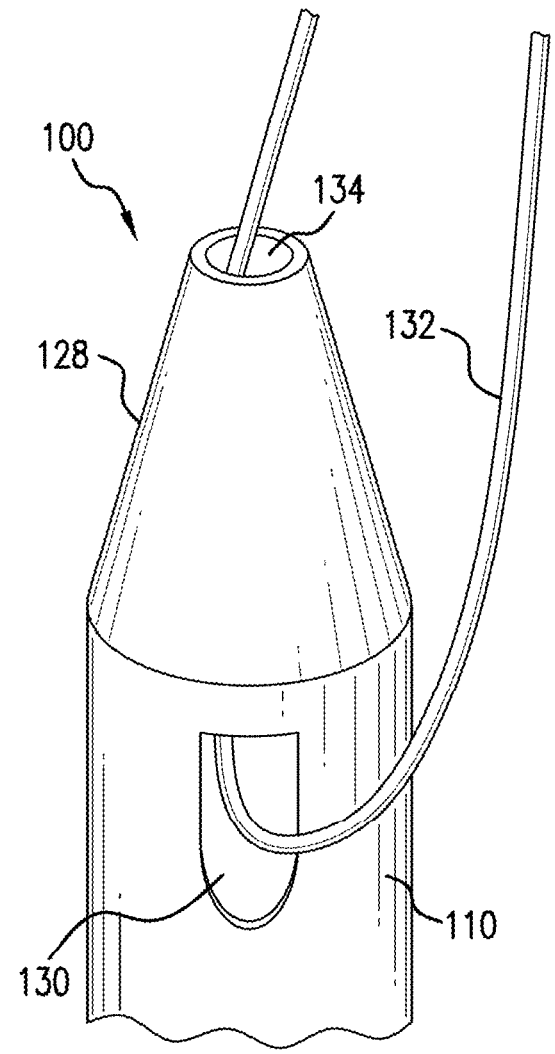
FIG. 7B is a close-up view of the second retention structure of the stent of FIG. 2 with a retrieval string through the eyelet.

This disclosure exploits this duality of indications by utilizing, as shown in FIG. 7A-7B, a tapered tip 128 with an eyelet 130 on coil 110 of second retention structure 106 that can be utilized in either of the above scenarios simply by inverting stent 100. FIG. 7B shows a retrieval string 132 through eyelet 130. When retrieval string 132 is desired, the surgeon simply passes a standard operating room suture through eyelet 130 and out of an opening 134 of stent 100. The surgeon can then tie the suture to itself to function as retrieval string 132.

Figure 8:
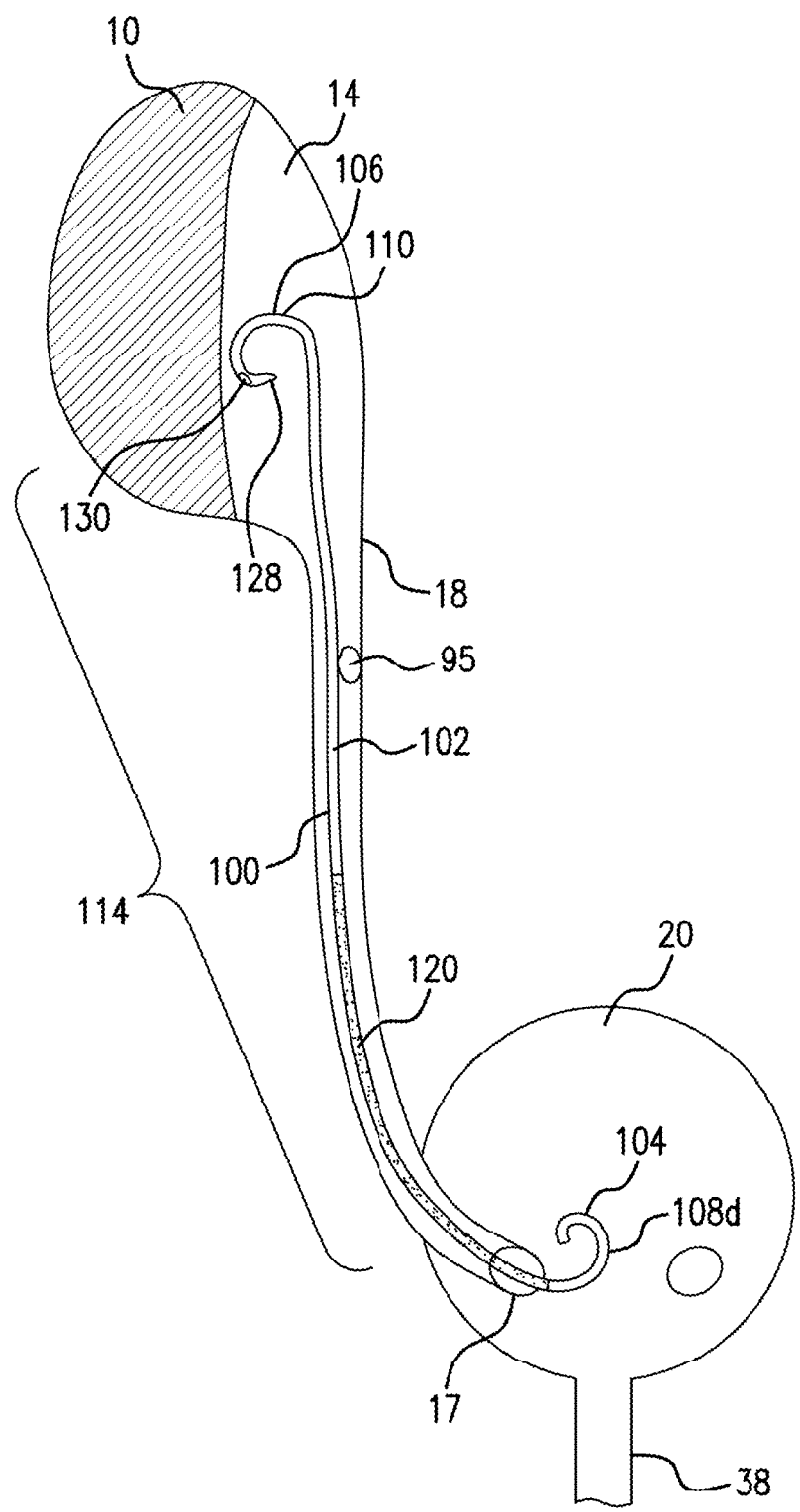
FIG. 8 shows a coronal view of the stent of FIG. 1 with the second retention structure positioned in a renal pelvis of a kidney and the first retention structure positioned in the bladder of a person.

FIG. 8 shows the deployment of second retention structure 106 with tapered tip 128 maneuvered beyond an obstructing stone 95 in ureter 18. In this case, there is no need for retrieval string 132 since stone 95 must be treated with a second procedure at a later date. Tapered tip 128 of second retention structure 106 is navigated beyond stone 95 and resides in renal pelvis 14.

Figure 9:
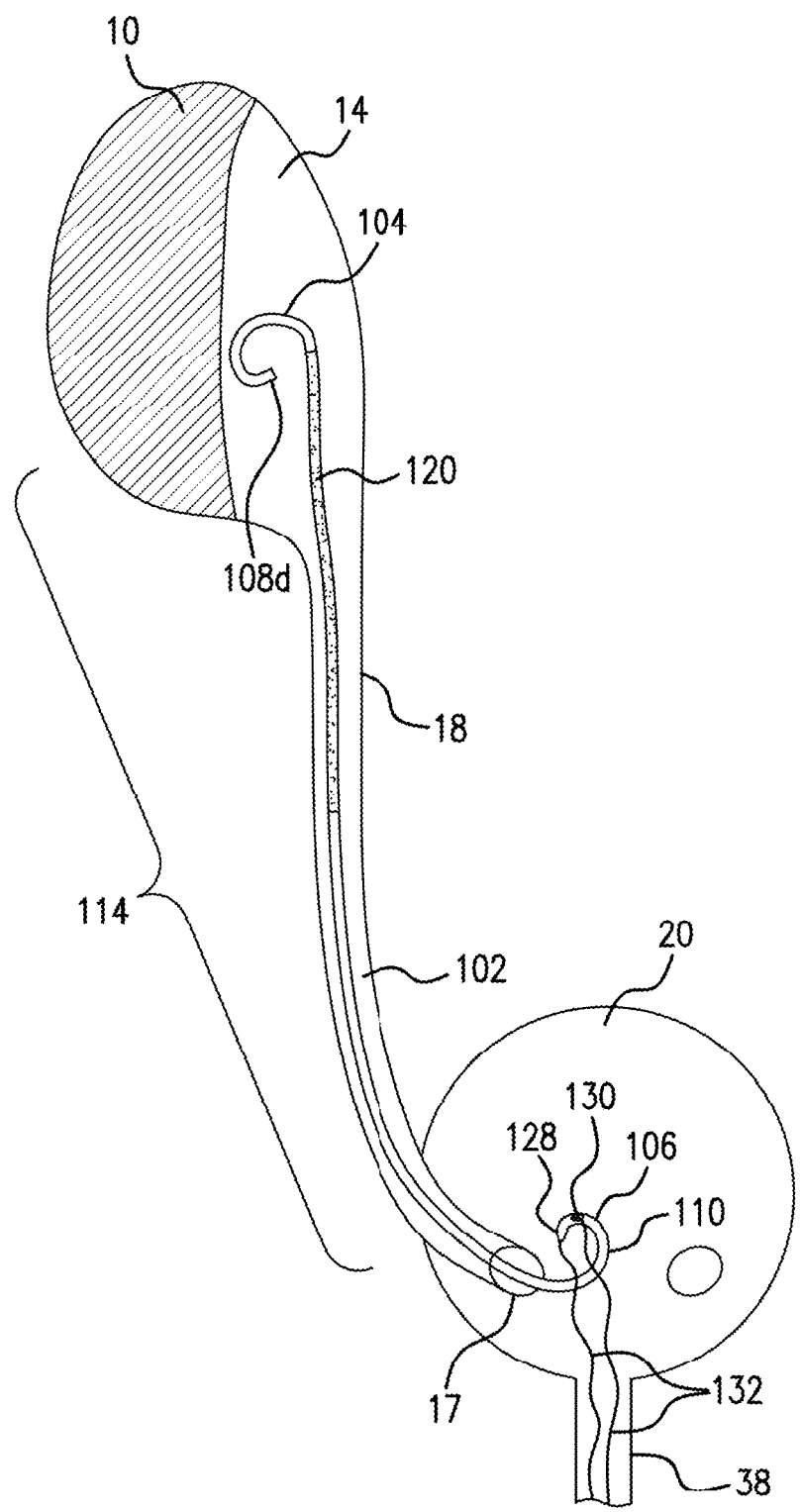
FIG. 9 shows a coronal view of the stent of FIG. 1 with the first retention structure positioned in a renal pelvis of a kidney and the second retention structure positioned in the bladder with a retrieval suture positioned through the eyelet of the second retention structure.

FIG. 9 shows the deployment of second retention structure 106 with tapered tip 128 after ureteroscopic manipulation. In this case, the primary obstructive process (ureteral stone 95) has been treated and stent 100 is left in place because postoperative ureteral swelling is anticipated. Tapered tip 128 is not needed to navigate stent 100 to renal pelvis 14, thus the physician places retrieval string 132 through eyelet 130 and out opening 134 on at the end of second retention structure 106 and places stent 100 in an inverted fashion with tapered tip 128 in the bladder 20. This dual tapered tip 128 and eyelet 130 feature addresses the benefit of a polarized stent design but allows one end of stent 100 to remain modifiable as discussed above.

Ureteral stent 100 can be formed of biocompatible shape memory tubing comprising a polymer, polyurethane, silicone, nitinol or other biocompatible material. Multiple coils 108 on first retention structure 104 can be straightened over a wire or forced to configure a coil shape directly opposing the desired orientation of multiple coils 108. While in this position, all or a portion of stent 100 is coated with anti-coiling layer 120 such that multiple coils 108 are completely straightened when stent 100 is in its native form. This creates elongated extension 122 extending from hollow tubular member 102 a longer length lacking without presenting an opposing coil until anti-coiling layer 120 is removed.

Anti-coiling polymer 120 can be a polymer, polyurethane, silicone, nitinol or any other type of biocompatible material that resists coiling. Stent 100 can include a thin exterior lubricous coating to facilitate the placement of the stent 100. The interior surface of hollow tubular member 102 could also be coated with a lubricous coating. Ureteral stent 100 can also include a series of drainage holes formed through tubular member 102 and at various locations thereby to admit urine or other fluids into a tubular member 102 for transport to bladder 20 past any obstruction in ureter 18.

The stent herein describe has a completely modifiable length and the ability to trim redundant stent material. This affords the physician the ability to intraoperatively place a stent of the ideal length, using a single product, for every patient. The invention also significantly decreases hospital stent inventory, since only varied stent diameter would need to be inventoried. It has the added benefit of being able to accommodate ureteral lengths at the extremes that almost universally are not inventoried by hospitals.

While this disclosure is directed to a stent 100 used in the ureter, one skilled in the art would recognize that the structure and methods disclosed herein relate to any type of drainage tubes used to divert fluid from viscus structures of the body and is applicable to any drainage tube where an adjustable length is desired. For simplicity, the main embodiment in the form of a ureteral stent is depicted and described. Other potential embodiments include other drainage devices used within viscus structures such as ventriculoperitoneal shunts, nephrostomy tubes, gastrostomy tubes, cholecystostomy tubes, etc.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

I claim:

1. A stent comprising:
   a tubular member comprising a first retention structure, a second retention structure and an intermediate section that extends therebetween in a continuous path, free of periodic curvature;
   wherein, the first retention structure at one end of the tubular member comprising multiple coils each of which has substantially the same diameter to provide an anchor for the stent;
   a removable anti-coiling material around the multiple coils of the first retention structure to present the multiple coils as an elongated extension of the tubular member, whereupon removal of the removable anti-coiling material at least one of the multiple coils of the first retention structure is presented;
   wherein, the second retention structure is at an opposite end of the tubular member; and
   a lumen extending through the tubular member, the first retention structure and the second retention structure.

2. A stent comprising:
   a tubular member comprising a first retention structure, a second retention structure and an intermediate straight section therebetween;
   wherein, the first retention structure at a distal end of the tubular member comprising multiple coils each of which has substantially the same diameter to provide an anchor for the stent;
   wherein, the second retention structure is at a proximal end of the tubular member; a lumen extending through the tubular member, the first retention structure and the second retention structure;
   a removable anti-coiling material around the multiple coils of the first retention structure to present the multiple coils as an elongated extension of the tubular member, whereupon removal of the removable anti-coiling material at least one of the multiple coils of the first retention structure is presented.

3. The stent of claim 2, and further comprising multiple indices on the elongated extension of the tubular member each of which demarcate a corresponding coil of the multiple coils of the first retention structure.

4. The stent of claim 3, wherein the multiple indices are each circumferential perforations in the anti-coiling material that enables a stripping away of the anti-coiling material.

5. The stent of claim 4, wherein the multiple indices are each visual markings.

6. The stent of claim 5, wherein the anti-coiling material is adapted for removal beginning from one of the multiple indices to an end of the elongated extension of the tubular member to present the at least one coil of the multiple coils of the first retention structure; and wherein one or more of the multiple coils is trimmable at a predetermined location to present a single coil of the multiple coils of the first retention structure.

7. The stent of claim 2, and further comprising a distal end on the second retention structure and a tapered tip on the distal end adapted for maneuvering the second retention structure past an obstruction.

8. The stent of claim 7, and further comprising an eyelet on the distal end of the tapered tip for receiving a suture.

9. The stent of claim 2, wherein each coil is wound about a separate axis.

10. A stent comprising:
    a tubular member;

a first retention structure and a second retention structure at opposite ends of the tubular member, wherein the first retention structure further comprises multiple coils each oriented in the same direction;

a lumen extending through the tubular member, the first retention structure, and the second retention structure, and further comprising an intermediate section between the first retention structure and the second retention structure that is physically continuous along its length, free of periodic curvature; and multiple indices on an elongated extension of the tubular member, each of which demarcate a corresponding one of the multiple coils of the first retention structure, wherein the multiple indices are each circumferential perforations in an anti-coiling material that enables a stripping away of the anti-coiling material.

11. The stent of claim 10 wherein each coil of the multiple coils is wound about a separate axis to provide an anchor for the stent.

12. The stent of claim 10, wherein the multiple indices are each visual markings.

13. The stent of claim 10, wherein the anti-coiling material is adapted for removal beginning from one of multiple indices to an end of the elongated extension of the tubular member to present at least the at least one coil of the multiple coils of the first retention structure, and wherein one or more of the multiple coils is trimmable at a predetermined location to present a single coil of the multiple coils of the first retention structure.

14. The stent of claim 10, and further comprising a distal end on the second retention structure and a tapered tip on the distal end.

15. The stent of claim 14, and further comprising an eyelet on the distal end of the tapered tip for receiving a suture.

16. The stent of claim 10, wherein each coil of the multiple coils is wound about a common axis to provide an anchor for the stent.

17. The stent of claim 2, wherein the removable anti-coiling material comprises of a biocompatible material that resists coiling.

18. The stent of claim 17, wherein the biocompatible material comprises a polymer.

19. The stent of claim 1, wherein the intermediate section is collinear with an axis extending through the lumen.

* * * * *